United States Patent [19]
Jonas et al.

[11] Patent Number: 6,143,777
[45] Date of Patent: Nov. 7, 2000

[54] AMINOTHIOPHENE CARBOXYLIC ACID AMIDES AND THE USE THEREOF AS PHOSPHODIESTERASE INHIBITORS

[75] Inventors: Rochus Jonas, Darmstadt; Pierre Schelling, Mühltal; Franz-Werner Kluxen, Darmstadt; Maria Christadler, Rödermark, all of Germany

[73] Assignee: Merck Patent Gesellschaft mit beschrankter Haftung, Germany

[21] Appl. No.: 09/284,501

[22] PCT Filed: Oct. 8, 1997

[86] PCT No.: PCT/EP97/05531

§ 371 Date: Apr. 14, 1999

§ 102(e) Date: Apr. 14, 1999

[87] PCT Pub. No.: WO98/16521

PCT Pub. Date: Apr. 23, 1998

[30] Foreign Application Priority Data

Oct. 15, 1996 [DE] Germany ............ 196 42 451

[51] Int. Cl.$^7$ ............ A61K 31/38; C07D 333/56; C07D 407/00; C07D 333/36
[52] U.S. Cl. ............ 514/447; 444/443; 549/57; 549/60; 549/69
[58] Field of Search ............ 549/57, 60, 69; 514/447, 444, 443

[56] References Cited

U.S. PATENT DOCUMENTS

| | | | |
|---|---|---|---|
| 5,075,310 | 12/1991 | Coates et al. | 514/258 |
| 5,356,926 | 10/1994 | Boschelli et al. | 514/445 |
| 5,504,213 | 4/1996 | Fischer et al. | 548/253 |
| 5,622,989 | 4/1997 | Braeunlich et al. | 514/469 |
| 5,712,304 | 1/1998 | Elbe et al. | 514/272.4 |
| 5,753,692 | 5/1998 | Chang et al. | 514/444 |
| 5,783,597 | 7/1998 | Beers et al. | 514/447 |
| 5,792,763 | 8/1998 | Fritz et al. | 514/228.2 |
| 5,807,889 | 9/1998 | Perregaard et al. | 514/469 |
| 5,863,936 | 1/1999 | Gaeta et al. | 514/443 |

FOREIGN PATENT DOCUMENTS

| | | |
|---|---|---|
| 349239 | 1/1990 | European Pat. Off. . |
| 623607 | 11/1994 | European Pat. Off. . |
| 685475 | 12/1995 | European Pat. Off. . |
| 4230755 | 3/1994 | Germany . |

OTHER PUBLICATIONS

DE4230755–English Abstract, 1994.

F. Sauter et al., "Neue Derivate der 2–Acylamino–thiophen (und benzo[b]thiophen)–3–carbonsaeure sowie des ([1]Benzo–)thieno[2,3–d]–pyrimidin–4–ons", Monatschrift Der Chemie, Bd. 107, Nr. 3, Mar. 1976, pp. 669–673, XP002055002.

Hussein, F. Zohdi et al., "Convenient heterocyclisation reactions with ethyl 2–amino–4,5,6,7–tetrahydrobenzo[b] thiophene–3–carboxylate", Journal of Chemical Research, Synopsis, No. 10, Oct. 1996, pp. 440–441, XP002055001.

*Primary Examiner*—Deborah C. Lambkin
*Attorney, Agent, or Firm*—Millen, White, Zelano & Branigan, P.C.

[57] ABSTRACT

Aminothiophenecarboxamides of the formula I

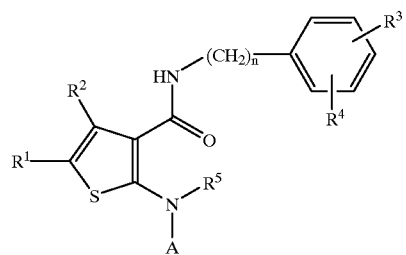

and their physiologically acceptable salts, wherein
$R^1$, $R^2$, $R^3$, $R^4$, $R^5$, A and n have the meanings stated in claim 1, exhibit phosphodiesterase V inhibition and can be used for the treatment of diseases of the cardiovascular system and for the therapy of disturbances of potency.

19 Claims, No Drawings

AMINOTHIOPHENE CARBOXYLIC ACID AMIDES AND THE USE THEREOF AS PHOSPHODIESTERASE INHIBITORS

This application is a 371 of PCT EP97/05531 Oct. 8, 1997.

The invention relates to compounds of the formula I

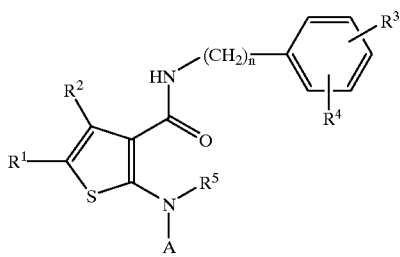

where
- $R^1$ and $R^2$, independently of one another, are each H, A, OA, alkenyl, alkynyl, $CF_3$ or Hal, one of the radicals $R^1$ or $R^2$ always being $\neq$ H,
- $R^1$ and $R^2$ together are also slkylene having 3–5 C atoms,
- $R^3$ and $R^4$, independently of one Another, are each H, A, OA, $NO_2$, $NH_2$ or Hal,
- $R^3$ and $R^4$ together are also —O—$CH_2$—$CH_2$—, —O—$CH_2$—O— or —O—$CH_2$—$CH_2$—O—,
- A and A', independently of one another, are each H or alkyl having 1 to 6 C atoms,
- $R^5$ is —X—Y,
- X is CO, CS or $SO_2$,
- Y is a saturated or unsaturated 5- to 7-membered isocyclic or heterocyclic ring which is unsubstituted or mono-substituted or disubstituted by COCH, COOA, $CONH_2$, CONAA', CONHA, CN, $NHSO_2A$, $Nd(SO_2A)_2$ or $SO_2A$,
- Hal is F, Cl, Br or I
and
- n is 0, 1, 2 or 3, and their physiologically acceptable salts.

It was the object of the invention to provide novel compounds having valuable properties, in particular those which can be used for the preparation of drugs.

It was found that the compounds of the formula I and their salts have very valuable pharmacological properties in combination with good tolerance.

In particular, they exhibit a specific inhibition of CGMP phosphodiesterase (PDE V).

Quinazolines having cGMP-phosphodiesterase-inhibiting activity are described, for example, in J. Med. Chem. 36, 3765 (1993) and ibid. 37, 2106 (1994). Pyrazolopyrimidones which are suitable for the treatment of disturbances of potency are described, for example, in WO 94/28902.

The biological activity of the compounds of the formula I can be determined by methods as described, for example, in WO 93/06104 or WO 94/28902. The affinity of the compounds according to the invention for cGMP- and cAMP-phosphodiesterase is determined by determining their $IC_{50}$ values (inhibitor concentration which is required to achieve 50% inhibition of the enzyme activity). Enzymes isolated by known methods can be used for carrying out the determinations (e.g. W. J. Thompson et al., Biochem. 1971, 10, 311) A modified "batch" method of W. J. Thompson and M. M. Appleman (Biochem. 1979, 18, 5228) can be used for carrying out the tests.

The compounds are therefore suitable for the treatment of diseases of the cardiovascular system, in particular of myocardial insufficiency, and for the therapy of disturbances of potency.

The compounds of the formula I can be used as drug active ingredients in human and veterinary medicine. Furthermore, they can be used as intermediates for the preparation of further drug active ingredients.

The invention accordingly relates to the compounds of the formula I and a process for the preparation of compounds of the formula I according to claim 1 and their salts, characterized in that a) a compound of the formula II

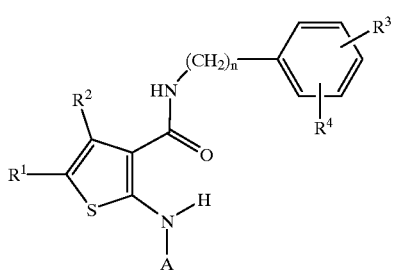

wherein
$R^1$, $R^2$, $R^3$, $R^4$ and n have the stated meanings,
is reacted with a compound of the formula III $$L—R^5 \quad \text{III}$$

wherein $R^5$ has the stated meaning and
L is Cl, Br, I, OH or an OH group rendered reactive by esterification, or b) a compound of the formula IV

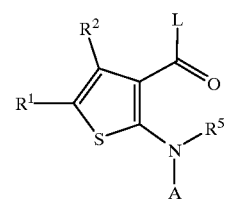

wherein
$R^1$, $R^2$, $R^5$ and A have the stated meanings
and L is Cl, Br, I, OH or an OH group rendered reactive by esterification,
is reacted with a compound of the formula V

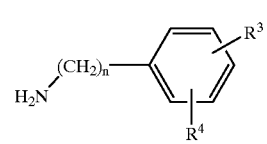

wherein
$R^3$, $R^4$ and n have the stated meanings, or c) in a compound of the formula I, a radical $R^3$, $R^4$ and/or $R^5$ is converted into another radical $R^3$, $R^4$ and/or $R^5$ by hydrolysing an ester or reducing a nitro group, and/or that an acid of the formula I is converted into one of its salts by treatment with a base.

Above and below, the radicals $R^1$, $R^2$, $R^3$, $R^4$, $R^5$, A, L and n have the meanings stated in the case of the formulae I, II, III, IV and V, unless expressly stated otherwise.

A and A' independently of one another are each preferably H or alkyl having 1–6 C atoms.

In the above formulae, alkyl is preferably straight-chain and has 1, 2, 3, 4, 5 or 6 C atoms, preferably 1, 2, 3, 4 or 5 C atoms, and is preferably methyl, ethyl or propyl, also preferably isopropyl, butyl, isobutyl, sec-butyl or tert-butyl, but also n-pentyl, neopentyl or isopentyl.

Alkylene is preferably straight-chain and is preferably propylene, butylene or pentylene.

Of the radicals $R^1$ and $R^2$, one is preferably H while the other is preferable propyl or butyl, but particularly preferably ethyl or methyl. Furthermore, $R^1$ and $R^2$ together are also preferably propylene, butylene or pentylene.

Hal is preferably F, Cl or Br, but also I.

Alkenyl is preferably vinyl, 1- or 2-propenyl, 1-butenyl, isobutenyl or sec-butenyl, 1-pentenyl, isopentenyl or 1-hexenyl also being preferred.

Alkynyl is preferably ethynyl, propyn-1-yl and furthermore butyn-1-yl, bityn-2-yl, pentyn-1-yl, pentyn-2-yl or pentyn-3-yl.

The radicals $R^3$ and $R^4$ may be identical or different and are preferably in the 3- or 4-position of the phenyl ring. They are, for example, independently of one another, each H, alkyl, alkoxy, nitro, amino, alkylamino, such as, for example, methylamino, dialkylamino, such as, for example, dimethylamino, F, Cl, Br or I, or together are ethyleneoxy, methylenedioxy or ethylenedioxy. They are each also preferably alkoxy, such as, for example, methoxy, ethoxy or propoxy.

The radical Y is preferably cyclopentyl, cyclohexyl, cycloheptyl, phenyl, 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl which is unsubstituted or monosubstituted or trisubstituted by COOH, COOCH$_3$, COOC$_2$H$_5$, CONH$_2$, CON(CH$_3$)$_2$, CONHCH$_3$, CN, NHSO$_2$CH$_3$, N(SO$_2$CH$_3$)$_2$ or SO$_2$CH$_3$, and is furthermore preferably 1,2,3-triazol-1-yl, 1,2,3-triazol-4-yl or 1,2,3-triazol-5-yl, 1,2,4-triazol-1-yl, 1,2,4-triazol-3-yl or 1,2,4-triazol-5-yl, 1- or 5-tetrazolyl, 1,2,3-oxadiazol-4-yl or 1,2,3-oxadiazol-5-yl, 1,2,4-oxadiazol-3-yl or 1,2,4-cxadiazol-5-yl, 1,3,4-thiadiazol-2-yl or 1,3,4-thiadiazol-5-yl, 1,2,4-thiadiazol-3-yl or 1,2,4-thiadiazol-5-yl, 1,2,3-thiadiazol-4-yl or 1,2,3-thiadiazol-5-yl, 3- or 4-pyridazinyl or pyrazinyl.

In particular, Y is, for example, 4-methoxycarbonylphenyl, 4-carboxyphenyl, 4-methoxycarbonylcyclohexyl, 4-carboxycyclohexyl, 4-methylsulphonamidophenyl, 4-methylsulphonamidocyclohexyl, 4-aminocarbonylphenyl or 4-aminocarbonylcyclohexyl.

X is preferably CO as well as CS or SO$_2$.

For the entire invention, it is true that all radicals which occur in a plurality may be identical or different, i.e. are independent of one another.

Accordingly, the invention relates in particular to those compounds of the formula I in which at least one of the stated radicals has one of the above mentioned preferred meanings. Some preferred groups of compounds can be expressed by the following partial formulae Ia to Ie, which correspond to the formula I and wherein the radicals not defined in more detail have the meaning stated in the case of formula I, but wherein in Ia Y is a phenyl or cyclohexyl ring which is unsubstituted or monosubstituted or disubstituted by COOH, COOA, CONH$_2$, CONAA', CONHA, CN, NHSO$_2$A, N(SO$_2$A)$_2$ or SO$_2$A;

in Ib $R^1$ and $R^2$ independently of one another are each H, A, OA, NO$_2$, CF$_3$ or Hal, at least one cf the radicals R or R always being≠H, $R^3$ and $R^4$ together are —O—CH$_2$—CH$_2$—, —O—CH$_2$—O— or —O—CH$_2$—CH$_2$—O, X is CO, Y is a phenyl or cyclohexyl ring which is unsubstituted or monosubstituted or disubstituted by COOH, COOA, CONH$_2$, CONAA', CONHA, CN, NHSO$_2$A, N(SO$_2$A)$_2$ or SO$_2$A and n is 1;

in Ic $R^1$ and $R^2$ independently of one another are each H, A, OA, NO$_2$, CF$_3$ or Hal, at least one of the radicals $R^1$ or $R^2$ always being≠H, $R^3$ and $R^4$ independently of one another are each H, A, OA, Hal, NO$_2$ or NH$_2$, X is CO, Y is a phenyl or cyclohexyl ring which is unsubstituted or monosubstituted or disubstituted by COOH, COOA, CONH$_2$, CONAA', CONHA, CN, NHSO$_2$A, N(SO$_2$A)$_2$ or SO$_2$A and n is 1;

in Id $R^1$ and $R^2$ together are alkylene having 3–5 C atoms, $R^3$ and $R^4$ together are —O—CH$_2$—CH$_2$—, —O—CH$_2$—O— or —O—CH$_2$—CH$_2$—O, X is CO, Y is a phenyl or cyclohexyl ring which is unsubstituted or monosubstituted or disubstituted by COOH, COOA, CONH$_2$, CONAA', CONHA, CN, NHSO$_2$A, N(SO$_2$A)$_2$ or SO$_2$A and n is 1;

in Ie $R^1$ and $R^2$ together are alkylene having 3–5 C atoms, $R^3$ and $R^4$ independently of one another are each H. A, OA, Hal, NO$_2$ or NH$_2$, X is CO, Y is a phenyl or cyclohexyl ring which is unsubstituted or monosubstituted or disubstituted by COOH, COOA, CONH$_2$, CONAA', CONHA, CN, NHSO$_2$A, N(SO$_2$A)$_2$ or SO$_2$A and n is 1.

The compounds of the formula I and also the starting materials for their preparation are furthermore prepared by methods known per se, as described in the literature (for example in the standard works such as Houben-Weyl, Methoden der organischen Chemie [Methods of organic chemistry], Georg-Thieme-Verlag, Stuttgart), the preparation being carried out under reaction conditions which are known and suitable for the stated reactions. It is also possible to make use of variants known per se and not mentioned in more detail here.

In the compounds of the formulae II, III, IV and V, $R^1$, $R^2$, $R^3$, $R^4$, $R^5$ and n have the stated meanings, in particular the stated preferred meanings.

If L is a reactive esterified OH group, it is preferably alkylsulphonyloxy having 1–6 C atoms (preferably methylsulphonyloxy) or arylsulphonyloxy having 6–10 C atoms (preferably phenyl- or p-tolylsulphonyloxy, and also 2-naphtalenesulphonyloxy).

The starting materials can, if desired, also be formed in situ so that they are not isolated from the reaction mixture but immediately further reacted to give the compounds of the formula I. On the other hand, it is possible to carry out the reaction stepwise.

The compounds of the formula I can preferably be obtained by reacting compounds of the formula II with compounds of the formula III.

Some of the starting materials of the formula II are known. Those which are not known can be prepared by methods known per se. The amides of the formula II are obtainable according to Houben-Weyl E6a, 320, from aldehydes or ketones and substituted cyanoacetamides in the presence of sulphur.

Specifically, the reaction of the compounds of the formula II with compounds of the formula III is carried out in the presence or absence of an inert solvent at temperatures between about −20 and about 150°, preferably between 20 and 100°.

The addition of an acici acceptor, for example an alkali metal or alkaline earth metal hydroxide, carbonate or bicarbonate or of another salt of a weak acid of the alkali metals or alkaline earth metals, preferably of potassium, of sodium or of calcium, or the addition of an organic base, such as triethylamine, dimethylamine, pyridine or quinioline, or of an excess of the amine component may be advantageous.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, iscpropanol, n-propanol, n-butanol or tert-butanol; ethers, such as diethyl ether, diisopropyl ether, tetrahydrofuran (THF) or dioxane; glycol ethers, such as ethylene glycol monomethyl ether or ethylene glycol monoethyl ether (methylglycol or ethylglycol), ethylene glycol dimethyl ether (diglyme); ketones, such as acetone or butanone; amides, such as acetamide, dimethylacetamide or dimethylformamide (DMF); nitriles, such as acetonitrile; sulphoxides, such as dimethyl sulphoxide (DYSO); nitro compounds, such as nitromethane or nitrobenzene; esters, such as ethyl acetate, or mixtures of the stated solvents.

Compounds of the formula I can furthermore be obtained by reacting compounds of the formula IV with compounds of the formula V. The starting compounds of the formulae IV and V are as a rule known. If they are not known, they can be prepared by methods known per se. The reaction of the compounds of the formula IV with compounds of the formula V is carried out, with regard to the reaction time, temperature and solvent, under conditions similar to those described for the reaction of the compounds of the formula II with the compounds of the formula III.

It is furthermore possible to convert a radical $R^3$ and/or $R^4$ in a compound of the formula I into another radical $R^3$ and/or $R^4$, for example by reducing nitro groups (for example by hydrogenation of a Raney nickel or Pd-carbon in an inert solvent, such as methanol or ethanol) to amino groups or hydrolysing cyano groups to COOH groups. COOA groups (an be hydrolysed, for example, with NaOH or KOH in water, water-THF or water-dioxane at temperatures between 0 and 100°. Furthermore, free amino groups can be acylated in the customary manner with an acid chloride or acid anhydride or alkylated with an unsubstituted or substituted alkyl halide, expediently in an inert. solvent, such as dichloromethane or THF, and/or in the presence of a base, such as triethylamine or pyridine, at temperatures between −60 and +30°.

An acid of the formula I can be converted with a base into the associated addition salt, for examples by reaction of equivalent amounts of the acid and of. the base in an inert solvent, such as ethanol, and subsequent concentration. Bases which give. physiologically acceptable salts are particularly suitable for this reaction. Thus, the acid of the formula I can be converted with a base (e.g. sodium or potassium hydroxide or carbonate) into the corresponding metal salt, in particular alkali metal or alkaline earth metal salt, or into the corresponding ammoniun salt.

On the other hand, a base of the formula I can be converted with an acid into the associated acid addition salt, for example by reaction of equivalent amounts of the base and of the acid in an inert solvent, such as ethanol, and subsequent concentration. Acids which give physiologically acceptable salts are particularly suitable for this reaction. It is therefore possible to use inorganic acids, e.g. sulphuric acid, nitric acid, hyclrohalic acids, such as hydrochloric acid or hydrobromic acid, phosphoric acids, such as orthophosphoric acid, or sulphamic acid, and organic acids, in particular aliphatic, alicyclic, araliphatic, aromatic or heterocyclic mono- or polybasic carboxylic, sulphonic or sulphuric acid, e.g. formic acid, acetic acid, propionic acid, pivalic acid, diethylacetic acid, malonic acid, succinic acid, pimelic acid, fumaric acid, maLeic acid, lactic acid, tartaric acid, malic acid, citzic acid, gluconic acid, ascorbic acid, nicotinic ac :d, isonicotinic acid, methane- or ethanesulphonic acid, ethanedisulphonic acid, 2-hydroxyethanesulphonic acid, benzenesulphonic acid, p-toluenesulphonic acid, naphthalenemonosulphonic and naphthalenedisulphonic aclds and laurylsulphuric acid. Salts with physiologically unacceptable acids, e.g. picrates, can be used for isolating and/or purifying the compounds of the formula I.

The invention furthermore relates to the use of the compounds of the formula I and/or their physiologically acceptable salts for the preparation of pharmaceutical formulations, in particular by a nonchemical method. Here, they can be brought into a suitable dosage form together with at least one solid, liquid and/or semiliquid vehicle or excipient and optionally in combination with one or more further active ingredients.

The invention also relates to drugs of the formula I and the physiologically acceptable salts as phosphodiesterase V inhibitors.

The invention furthermore relates to pharmaceutical formulations comprising at least one compound of the formula I and/or one of its physiologically acceptable salts.

These formulations can be used as drugs in human or veterinary medicine. Suitable vehicles are organic or inorganic substances which are suitable for enteral (e.g. oral), parenteral or topical application and do not react with the novel compounds, for example water, vegetable oils, benzyl alcohols, alkylene glycols, polyethylene glycols, glycerol triacetate, gelatine, carbohydrates, such as lactose or starch, magnesium stearate, talc and vaseline. In particular, tablets, pills, coated tablets, capsules, pellets, granules, syrups, elixirs or drops serve for oral use, suppositories for rectal use, solutions, preferably oily or aqueous solutions, ana suspensions, emulsions or implants for parenteral use, and ointments, creams or powders for topical use. The novel compounds can also be lyophilized and the lyophilisates obtained can be used, for example, for the production of injection preparations. The stated formulations may be sterilized and/or may comprise excipients, such as lubricants, preservatives, stabilizers and/or wetting agents, emulsifiers, salts for influencing the osmotic pressure, buffer substances, colorants, flavours and/or several other active ingredients, for example one or more vitamins.

The compounds of the formula I and their physiologically acceptable salts can be used in the treatment of diseases where an increase in the cGMP (cyclo-guanosine monophosphate) level leads to inhibition or prevention of inflammation and muscular relaxation. The compounds according to the invention are used in particular in the treatment of diseases of the cardiovascular system and for the therapy of disturbances of potency.

The substances are administered, as a rule, preferably in doses between about 1 and 500 mg, in particular about 5 and 100 mg, per dosage unit. The daily dose is preferably between about 0.02 and 10 mg/kg body weight. However, the specific dose for each patient depends on a very wide range of factors, for example on the efficacy of the specific compound used, on the age, body weight, general state of health and sex, on the diet, on the time and route of administration and on the excretion rate, drug combination and severity of the respective disease for which the therapy is used. Oral application is preferred.

Above and below, all temperatures are stated in ° C. In the Examples below, "customary working-up" means: if required water is added, if required the pH is adjusted to values between 2 and 10, depending on the constitution of the end product, extraction is carried out with ethyl acetate and dichloromethane, the phases are separated, the organic phase is dried over sodium sulphate, concentrated and purified by chromatography over silica gel and/or by crystallization.

Mass spectrometry (MS): EI (electron impact ionization); $M^+$; FAB (Fast Atom Bombardment); $(M+H)^+$

EXAMPLE 1

1.0 g of methoxycarbonylbenzoyl chloride ("A") is added to a solution of 1.5 g of N-(benzo[1,3]dioxol-5-ylmethyl)-2-amino-4,5,6,7-tetrahydrobenzo[b]thiophene-3-carboxamide [obtainable by reacting cyclohexanone with N-benzo[1,3]dioxol-5-ylmethyl-2-cyanoacetamide in the presence of sulphur) in 50 ml of dichloromethane and 2 ml of pyridine and stirring is carried out for 2 hours at room temperature. The solvent is removed and is worked up in the customary manner. 1.3 g of methyl 4-{3-[(benzo[1,3]dioxol-5-ylmethyl)carbamoyl]-4,5,6,7-tetrahydrobenzo[b]thiophene-2-ylcarbamoyl}benzoate, m.p. 165°, are obtained.

In an analogous manner, reaction of "A"
with N-(benzo[1,3]dioxol-5-ylmetlyl)-2-amino-5-methylthiophene-3-carboxamide gives
   methyl 4-{3-[(benzo[1,3]dioxol-5-ylmethyl)carbamoyl]-5-methylthiophen-2-ylcarbamoyl}benzoate, m.p. 138°;
with N-(benzo[1,3]dioxol-5-ylmethyl)-2-amino-5,6-dimethylthiophene-3-carboxamide gives
   methyl 4-{3-[(benzo[1,3]dioxol-5-ylmethyl)carbamoyl]-5,6-dimethylthiophen-2-ylcarbamoyl}benzoate;
with N-(benzo[1,3]dioxol-5-ylmethyl)-2-amino-5-chlorothiophene-3-carboxamide gives
   methyl 4-{3-[(benzo[1,3]dioxol-5-ylmethyl)carbamoyl]-5-chlorothiophen-2-ylcarbamoyl}benzoate;
with N-(benzo[1,3]dioxol-5-ylmethyl)-2-amino-4,5-cyclopentenothiophene-3-carboxamide gives
   methyl 4-{3-[(benzo[1,3]dioxol-5-ylmethyl)carbamoyl]-4,5-cyclopentencthiophen-2-ylcarbamoyl}benzoate;
with N-(benzo[1,3]dioxol-5-ylmethyl)-2-amino-4,5-cycloheptenothiophene-3-carboxamide gives
   methyl 4-{3-[(benzo)[1,3]dioxol-5-ylmethyl)carbamoyl]-4,5-cycloheptenothiophen-2-ylcarbamoyl}benzoate;
with N-(benzol1,3]dioxol-5-ylmethyl)-2-amino-5-ethylthiophene-3-carboxamide gives
   methyl 4-{3-[(benzo[1,3]dioxol-5-ylmethyl)carbamoyl]-5-ethylthiophen-2-ylcarbamoyl}benzoate;
with N-(benzo[1,3]dioxol-5-ylmethyl)-2-amino-5-propylthiophene-3-carboxamide gives
   methyl 4-{3-[(benzo[1,3]dioxol-5-ylmethyl)carbamoyl]-5-propylthiophen-2-ylcarbamoyl}benzoate;
with N-(benzo[1,3]dioxol-5-ylmethyl)-2-amino-5-isopropylthiophene-3-carboxamide gives
   methyl 4-{3-[(benzo[1,3]dioxol-5-ylmethyl)carbamoyl]-5-isopropylthiophen-2-ylcarbamoyl}benzoate;
with N-(benzo[1,3]dioxol-5-ylmethyl)-2-amino-5-butylthiophene-3-carboxamide gives
   methyl 4-{3-[(benzo[1,3]dioxol-5-ylmethyl)carbamoyl]-5-butylthiophen-2-ylcarbamoyl}benzoate;
with N-benzyl-2-amino-4,5,6,7-tetrahydrobenzo[b]thiophene-3-carboxamide gives
   methyl 4-[3-(benzylcarbamoyl)-4,5,6,7-tetrahydrobenzo[b]thiophen-2-ylcarbamoyl]benzoate;
with N-benzyl-2-amino-5-methylthiophene-3-carboxamide gives
   methyl 4-[3-(benzylcarbamoyl)-5-methylthiophen-2-ylcarbamoyl]benzoate, m.p. 170°;
with N-benzyl-2-amino-5-isopropylthiophene-3-carboxamide gives
   methyl 4-[3-(benzylcarbamoyl)-5-isopropylthiophen-2-ylcarbamoyl]benzoate, m.p. 170–172°;
with N-benzyl-2-amino-5-chlorothiophene-3-carboxamide gives
   methyl 4-[3-(benzylcarbamoyl)-5-chlorothiophen-2-ylcarbamoyl]benzoate;
with N-benzyl-2-amino-4,5-cyclopentenothiophene-3-carboxamide gives
   methyl 4-[3-(benzylcarbamoyl)-4,5-cyclopentenothiophen-2-ylcarbamoyl]benzoate;
with N-benzyl-2-amino-4,5-cycloheptenothiophene-3-carboxamide gives
   methyl 4-[3-(benzylcarbsmoyl)-4,5-cycloheptenothiophen-2-ylcarbamoyl]benzcate;
with N-benzyl-2-amino-5-ethylthiophene-3-carboxamide gives
   methyl 4-[3-(benzylcarbamoyl)-5-ethylthiophen-2-ylcarbamoyl]benzoate;
with N-(3-chloro-4-methoxybenzyl)-2-amino-4,5,6,7-tetrahydrobenzo[b]thiophene-3-carboxamide gives
   methyl 4-{3-[(3-chloro-4-methoxybenzyl)carbamoyl]-4,5,6,7-tetrahydrobenzo[b]thiophen-2-ylcarbamoyl}benzoate;
with N-(3-choro-4-methoxybenzyl)-2-amino-5-methylthiophene-3-carboxamide gives
   methyl 4-{3-[(3-chloro-4-methoxybenzyl)carbamoyl]-5-methylthiophen-2-ylcarbamoyl}benzoate;
with N-(3-chloro-4-methoxybenzyl)-2-amino-5-chlorothiophene-3-carboxamide gives
   methyl 4-{3-[(3-chloro-4-me-hoxybenzyl)carbamoyl]-5-chlorothiophen-2-ylcarbamoyl}benzoate;
with N-(3-chloro-4-methoxybenzyl)-2-amino-4,5-cyclopentenothiophene-3-carboxamide gives
   methyl 4-{3-[(3-chloro-4-methoxybenzyl)carbamoyl]-4,5-cyclopentenothiophen-2-ylcarbamoyl}benzoate;
with N-(3-chloro-4-methoxybenzyl)-2-amino-4,5-cycloheptenothiophene-3-carboxamide gives
   methyl 4-{3-[(3-chloro-4-methoxybenzyl)carbamoyl]-4,5-cycloheptenothiophen-2-ylcarbamoyl}benzoate;
with N-(3-chloro-4-methoxybenzyl)-2-amino-5-ethylthiophene-3-carboxamide gives methyl 4-{3-[(3-chloro-4-methoxybenzyl)carbamoyl]-5-ethylthiophen-2-ylcarbamoyl}benzoate;
with N-(3,4-dimethoxybenzyl)-2-amino-4,5,6,7-tetrahydrobenzo[b]thiophene-3-carboxamide gives
  methyl 4-{3-[(3,4-dimethoxybenzyl)carbamoyl]-4,5,6,7-tetrahydrobenzo[b]thiophen-2-ylcarbamoyl}benzoate;
with N-(3,4-dimethoxybenzyl)-2-amino-5-methylthiophene-3-carboxamide gives
  methyl 4-[3-[(3,4-dimethoxybenzyl)carbamoyl]-5-methylthiophen-2-ylcarbamoyl}benzoate, m.p. 175°;
with N-(3,4-dimethoxybenzyl)-2-amino-5-chlorothiophene-3-carboxamide gives
  methyl 4-{3-[(3,4-dimethoxybenzyl)carbamoyl]-5-chlorothiophen-2-ylcarbamoyl}benzoate;
with N-(3,4-dimethoxybenzyl)-2-amino-4,5-cyclopentenothiophene-3-carboxamide gives
  methyl 4-{3-[(3,4-dimethoxybenzyl)carbamoyl]-4,5-cyclopentenothiophen-2-ylcarbamoyl}benzoate;
with N-(3,4-dimethoxybenzyl)-2-amino-4,5-cycloheptenothiophene-3-carboxamide gives
  methyl 4-{3-[(3,4-dimethoxybenzyl)carbamoyl]-4,5-cycloheptenothiophen-2-ylcarbamoyl}benzoate;
with N-(3,4-dimethoxybenzyl)-2-amino-5-ethylthiophene-3-carboxamide gives
  methyl 4-{3-[(3,4-dimethoxybenzyl)carbamoyl]-5-ethylthiophen-2-ylcarbamoyl}benzoate;
with N-(4-fluorobenzyl)-2-amino-4,5,6,7-tetrahydro[b]thiopen-3-carboxamide gives
  methyl 4-{3-[(4-fluorobenzyl)carbamoyl]-4,5,6,7-tetrahydrobenzo[b]thiophen-2-ylcarbamoyl}benzoate;
with N-(4-fluorobenzyl)-2-amino-5-methylthiophene-3-carboxamide gives
  methyl 4-{3-[(4-fluorobenzyl)carbamoyl]-5-methylthiophen-2-ylcarbamoyl}benzoate;
with N-(4-fluorobenzyl)-2-amino-5-chlorothiophene-3-carboxamide gives
  methyl 4-{3-[(4-fluorobenzyl)carbamoyl]-5-chlorothiophen-2-ylcarbamoyl}benzoate;
with N-(4-fluorobenzyl)-2-amino-4,5-cyclopentenothiophene-3-carboxamide gives
  methyl 4-{3-[(4-fluorobenzyl)carbamoyl]-4,5-cyclopentenothiophen-2-ylcarbamoyl}benzoate;
with N-(4-fluorobenzyl)-2-amino-4,5-cycloheptenothiophene-3-carboxamide gives
  methyl 4-{3-[(4-fluorobenzyl)carbamoyl]-4,5-cycloheptenothiophen-2-ylcarbamoyl}benzoate;
with N-(4-fluorobenzyl)-2-amino-5-ethylthiophene-3-carboxamide gives
  methyl 4-{3-[(4-fluorobenzyl)carbamoyl]-5-ethylthiophen-2-ylcarbamoyl}benzoate;
with N-(3-nitrobenzyl)-2-amino-4,5,6,7-tetrahydrobenzo[b]thiophene-3-carboxamide gives
  methyl 4-{3-[(3-nitrobenzyl)carbamoyl]-4,5,6,7-tetrahydrobenzo[b]thiophen-2-ylcarbamoyl}benzoate;
with N-(3-nitrobenzyl)-2-amino-5-methylthiophene-3-carboxamide gives
  methyl 4-{3-[(3-nitrobenzyl)carbamoyl]-5-methylthiophen-2-ylcarbamoyl}benzoate;
with N-(3-nitrobenzyl)-2-amino-5-chlorothiophene-3-carboxamide gives
  methyl 4-{3-[(3-nitrobenzyl)carbamoyl]-5-chlorothiophen-2-ylcarbamoyl}benzoate;
with N-(3-nitrobenzyl)-2-amino-4,5-cyclopentenothiophene-3-carboxamide gives
  methyl 4-{3-[(3-nitrobenzyl)carbamoyl]-4,5-cyclopentenothiophen-2-ylcarbamoyl}benzoate;
with N-(3-nitrobenzyl)-2-amino-4,5-cycloheptenothiophene-3-carboxamide gives
  methyl 4-{3-[(3-nitrobenzyl)carbamoyl]-4,5-cycloheptenothiophen-2-ylcarbamoyl}benzoate;
with N-(3-nitrobenzyl)-2-amino-5-ethylthiophene-3-carboxamide gives
  methyl 4-{3-[(3-nitrobenzyl)carbamoyl]-5-ethylthiophen-2-ylcarbamoyl}benzoate;
with N-phenethyl-2-amino-4,5,6,7-tetrahydrobenzo[b]thiophene-3-carboxamide gives
  methyl 4-[3-(phenethylcarbamoyl)-4,5,6,7-tetrahydrobenzo[b]thiophen-2-ylcarbamoyl}benzoate;
with N-phenethyl-2-amino-5-methylthiophene-3-carboxamide gives
  methyl 4-[3-(phenethylcarbamoyl)-5-methylthiophen-2-ylcarbamoyl}benzoate;
with N-phenethyl-2-amino-5-chlorothiophene-3-carboxamide gives
  methyl 4-[3-(phenethylcarbamoyl)-5-chlorothiophen-2-ylcarbamoyl}benzoate;
with N-phenethyl-2-amino-4,5-cyclopentenothiophene-3-carboxamide gives
  methyl 4-[3-(phenethylcarbamoyl)-4,5-cyclopentenothiophen-2-ylcarbamoyl]benzoate;
with N-phenethyl-2-amino-4,5-cycloheptenothiophene-3-carboxamide gives
  methyl 4-[3-(phenethylcarbamoyl)-4,5-cycloheptenothiophen-2-ylcarbamoyl]benzoate;
with N-phenethyl-2-amino-5-ethylthiophene-3-carboxamide gives
  methyl 4-[3-(phenethylcarbamoyl)-5-ethylthiophen-2-ylcarbamoyl]benzoate.

EXAMPLE 2

Analogously to Example 1, the reaction of N-(benzo[1,3]dioxol-5-ylmethyl)-2-amino-4,5,6,7-tetrahydrobenzo[b]thiophene-3-carboxamide with 4-methoxycarbonylcyclohexanecarbonyl chloride ("B") gives the compound methyl 4-{3-[(benzo[1,3]dioxol-5-ylmethyl)carbamoyl]-4,5,6,7-tetrahydrobenzo[b]thiophen-2-ylcarbamoyl}cyclohexanecarboxylate, m.p. 173°.

In an analogous manner, reaction of "B" with N-(benzo[1,3]dioxol-5-ylmethyl)-2-amino-5-methylthiophene-3-carboxamide gives
  methyl 4-{3-[(benzo[1,3]dioxol-5-ylmethyl)carbamoyl]-5-methylthiophen-2-ylcarbamoyl}cyclohexanecarboxylate, oil;
with N-(benzo[1,3]dioxol-5-ylmethyl)-2-amino-5,6-dimethylthiophene-3-carboxamide gives
  methyl 4-{3-[(benzo 1,3]dioxol-5-ylmethyl)carbamoyl]-5,6-dimethylthiophen-2-ylcarbamoyl}cyclohexanecarboxylate;
with N-(benzo[1,3]dioxol-5-ylmethyl)-2-amino-5-chlorothiophene-3-carboxamide gives
  methyl 4-{3-[(benzo[1,3]dioxol-5-ylmethyl)carbamoyl]-5-chlorothiophen-2-ylcarbamoyl}cyclohexanecarboxylate;
with N-(benzo[3]dioxol-5-ylmethyl)-2-amino-4,5-cyclopentenothiophene-3-carboxamide gives
  methyl 4-{3-[(benzo[1,3]dioxol-5-ylmethyl)carbamoyl]-4,5-cyclopentenothiophen-2-ylcarbamoyl}cyclohexanecarboxylate;

with N-(benzo[1,3]dioxol-5-ylmethyl)-2-amino-4,5-cycloheptenothiophene-3-carboxamide gives
    methyl 4-{3-[(benzo[1,3]dioxol-5-ylmethyl)carbamoyl]-4,5-cycloheptenothiophen-2-ylcarbamoyl}cyclohexanecarboxylate;
with N-(benzo[1,3]dioxol-5-ylmethyl)-2-amino-5-ethylthiophene-3-carboxamide gives
    methyl 4-{3-[(benzo[1,3]dioxol-5-ylmethyl)carbamoyl]-5-ethylthiophen-2-ylcarbamoyl}cyclohexanecarboxylate, oil;
with N-benzyl-2-amino-4,5,6,7-tetrahydrobenzo[b]thiophene-3-carboxamide gives
    methyl 4-[3-(benzylcarbamoyl)-4,5,6,7-tetrahydrobenzo[b]thiophen-2-ylcarbamoyl]cyclohexanecarboxylate;
with N-benzyl-2-amino-5-methylthiophene-3-carboxamide gives
    methyl 4-[3-(benzylcarbamoyl)-5-methylthiophen-2-ylcarbamoyl]cyclohexanecarboxylate;
with N-benzyl-2-amino-5-chlorothiophene-3-carboxamide gives
    methyl 4-[3-(benzylcarbamoyl)-5-chlorothiophen-2-ylcarbamoyl]cyclohexanecarboxylate;
with N-benzyl-2-amino-4,5-cylopentenothiophene-3-carboxamide gives
    methyl 4-[3-(benzylcarbamoyl)-4,5-cyclopentenothiophen-2-ylcarbamoyl]cyclohexanecarboxylate;
with N-benzyl-2-amino-4,5-cycloheptenothiophene-3-carboxamide gives
    methyl 4-[3-(benzylcarbamoyl)-4,5-cycloheptenothiophen-2-ylcarbamoyl]cyclohexanecarboxylate;
with N-benzyl-2-amino-5-ethylthiophene-3-carboxamide gives
    methyl 4-[3-(benzylcarbamoyl)-5-ethylthiophen-2-ylcarbamoyl]cyclohexanecarboxylate;
with N-(3-chloro-4-methoxybenzyl)-2-amino-4,5,6,7-tetrahydrobenzo[b]thiophene-3-carboxamide gives
    methyl 4-{3-[(3-chloro-4-methoxybenzyl)carbamoyl]-4,5,6,7-tetrahydrobenzo[b]thiophen-2-ylcarbamoyl}cyclohexanecarboxylate;
with N-(3-chloro-4-methoxybenzyl)-2-amino-5-methylthiophene-3-carboxamide gives
    methyl 4-{3-[(3-chloro-4-methoxybenzyl)carbamoyl]-5-methylthiophen-2-ylcarbamoyl}cyclohexanecarboxylate;
with N-(3-chloro-4-methoxybenzyl)-2-amino-5-chlorothiophene-3-carboxamide gives
    methyl 4-{3-[(3-chloro-4-methoxybenzyl)carbamoyl]-5-chlorothiophen-2-ylcarbamoyl}cyclohexanecarboxylate;
with N-(3-chloro-4-methoxybenzyl)-2-amino-4,5-cyclopentenothiophene-3-carboxamide gives
    methyl 4-{3-[(3-chloro-4-methoxybenzyl)carbamoyl]-4,5-cyclopentenothiophen-2-ylcarbamoyl}cyclohexanecarboxylate;
with N-(3-chloro-4-methoxybenzyl)-2-amino-4,5-cycloheptenothiophene-3-carboxamide gives
    methyl 4-{3-[(3-chloro-4-methoxybenzyl)carbamoyl]-4,5-cycloheptenothiophen-2-ylcarbamoyl}cyclohexanecarboxylate;
with N-(3-chloro-4-methoxybenzyl)-2-amino-5-ethylthiophene-3-carboxamide gives
    methyl 4-{3-[(3-chloro-4-methoxybenzyl)carbamoyl]-5-ethylthiophen-2-ylcarbamoyl}cyclohexanecarboxylate;
with N-(3,4-dimethoxybenzyl)-2-amino-4,5,6,7-tetraydrobenzo[b]thiophene-3-carboxamide gives
    methyl 4-{3-[(3,4-dimethoxybenzyl)carbamoyl]-4,5,6,7-tetrahydrobenzo[b]thiophen-2-ylcarbamoyl}cyclohexanecarboxylate;
with N-(3,4-dimethoxybenzyl)-2-amino-5-methylthiophene-3-carboxamide gives
    methyl 4-{3-[(3,4-dimethoxybenzyl)carbamoyl]-5-methylthiophen-2-ylcarbamoyl}cyclohexanecarboxylate;
with N-(3,4-dimethoxybenzyl)-2-amino-5-chlorothiophene-3-carboxamide gives
    methyl 4-{3-[(3,4-dimethoxybenzyl)carbamoyl]-5-chlorothiophen-2-ylcarbamoyl}cyclohexanecarboxylate;
with N-(3,4-dimethoxybenzyl)-2-amino-4,5-cyclopentenothiophene-3-carboxamide gives
    methyl 4-{3-[(3,4-dimethoxybenzyl)carbamoyl]-4,5-cyclopentenothiophen-2-ylcarbamoyl}cyclohexanecarboxylate;
with N-(3,4-dimethoxybenzyl)-2-amino-4,5-cycloheptenothiophene-3-carboxamide gives
    methyl 4-{3-[(3,4-dimethoxybenzyl)carbamoyl]-4,5-cycloheptenothiophen-2-ylcarbamoyl}cyclohexanecarboxylate;
with N-(3,4-dimethoxybenzyl)-2-amino-5-ethylthiophene-3-carboxamide gives
    methyl 4-{3-[(3,4-dimethoxybenzyl)carbamoyl]-5-ethylthiophen-2-ylcarbamoyl}cyclohexanecarboxylate;
with N-(4-fluorobenzyl)-2-amino-4,5,6,7-tetrahydrobenzo[b]thiophene-3-carboxamide gives
    methyl 4-{3-[(4-fluorobenzyl)carbamoyl]-4,5,6,7-tetrahydrobenzo[b]thiophen-2-ylcarbamoyl}cyclohexanecarboxylate;
with N-(4-fluorobenzyl)-2-amino-5-methylthiophene-3-carboxamide gives
    methyl 4-{3-[(4-fluorobenzyl)carbamoyl]-5-methylthiophen-2-ylcarbamoyl}cyclohlexanecarboxylate;
with N-(4-fluorobenzyl)-2-amino-5-chlorothiophene-3-carboxamide gives
    methyl 4-{3-[(4-fluorobenzyl)carbamoyl]-5-chlorothiophen-2-ylcarbamoyl}cyclohexanecarboxylate;
with N-(4-chlorobenzyl)-2-amino-4,5-cyclopentenothiophene-3-carboxamide gives
    methyl 4-{3-[(4-fluorobenzyl)carbamoyl]-4,5-cyclopentenothiophen-2-ylcarbamoyl}cyclohexanecarboxylate;
with N-(4-fluorobenzyl)-2-amino-4,5-cycloheptenothiophene-3-carboxamide gives
    methyl 4-{3-[(4-fluorobenzyl)carbamoyl]-4,5-cycloheptenothiophen-2-ylcarbamoyl}cyclohexanecarboxylate;
with N-(4-fluorobenzyl)-2-amino-5-ethylthiophene-3-carboxamide gives
    methyl 4-{3-[(4-fluorobenzyl)carbamoyl]-5-ethylthiophen-2-ylcarbamoyl}cyclohexanecarboxylate;
with N-(3-nitrobenzyl)-2-amino-4,5,6,7-tetrahydrobenzo[b]thiophene-3-carboxamide gives
    methyl 4-{3-[(3-nitrobenzyl)carbamoyl]-4,5,6,7-tetrahydrobenzo[b]thiophen-2-ylcarbamoyl}cyclohexanecarboxylate;

with N-(3-nitrobenzyl)-2-amino-5-methylthiophene-3-carboxamide gives methyl 4-{3-[(3-nitrobenzyl)carbamoyl]-5-methylthiophen-2-ylcarbamoyl}cyclohexanecarboxylate;

with N-(3-nitrobenzyl)-2-amino-5-chlorothiophene-3-carboxamide gives methyl 4-{3-[(3-nitrobenzyl)carbamoyl]-5-chlorothiophen-2-ylcarbamoyl}cyclohexanecarboxylate;

with N-(3-nitrobenzyl)-2-amino-4,5-cyclopentenothiophene-3-carboxamide gives methyl 4-{3-[(3-nitrobenzyl)carbamoyl]-4,5-cyclopentenothiophen-2-ylcarbamoyl}cyclohexanecarboxylate;

with N-(3-nitrobenzyl)-2-amino-4,5-cycloheptenothiophene-3-carboxamide gives methyl 4-{3-[(3-nitrobenzyl)carbamoyl]-4,5-cycloheptenothiophen-2-ylcarbamoyl}cyclohexanecarboxylate;

with N-(3-nitrobenzyl)-2-amino-5-ethylthiophene-3-carboxamide gives methyl 4-{3-[(3-nitrobenzyl)carbamoyl]-5-ethylthiophen-2-ylcarbamoyl}cyclohexanecarboxylate;

with N-phenethyl-2-amino-4,5,6,7-tetrahydrobenzo[b]thiophene-3-carboxamide gives methyl 4-[3-(phenylethylcarbamoyl)-4,5,6,7-tertrahydrobenzo[b]thiophen-2-ylcarbamoyl]cyclohexanecarboxylate;

with N-phenethyl-2-amino-5-methylthiophene-3-carboxamide gives methyl 4-[3-(phenethylcarbamoyl)-5-methylthiophen-2-ylcarbamoyl]cyclohexanecarboxylate;

with N-phenethyl-2-amino-5-chlorothiophene-3-carboxamide gives methyl 4-[3-(phenethylcarbamoyl)-5-chlorothiophen-2-ylcarbamoyl]cyclohexanecarboxylate;

with N-phenethyl-2-amino-4,5-cyclopentenothiophene-3-carboxamide gives methyl 4-[3-(phenethylcarbamoyl)-4,5-cyclopentenothiophen-2-ylcarbamoyl]cyclohexanecarboxylate;

with N-phenethyl-2-amino-4,5-cycloheptenothiophene-3-carboxamide gives methyl 4-[3-(phenethylcarbamoyl)-4,5-cycloheptenothiophen-2-ylcarbamoyl]cyclohexanecarboxylate;

with N-phenethyl-2-amino-5-ethylthiophene-3-carboxamide gives methyl 4-(3-(phenethylcarbamoyl)-5-ethylthiophen-2-ylcarbamoyl]cyclohexanecarboxylate.

EXAMPLE 3

Methyl 4-(3-chlorocarbonyl-4,5,6,7-tetrahydrobenzo[b]thiophen-2-ylcarbamoyl)benzoate is added to a solution of (benzo[1,3]dioxol-5-ylmethyl)amine in dichloromethane and 1.1 equivalents of pyridine and the solution is stirred. The solvent is removed and is worked up in a customary manner. 1.3 g of methyl 4-{3[(benzo[1,3]dioxol-5-ylmethyl)carbamoyl]-4,5,6,7-tetrahydrobenzo[b]thiophene-2-ylcarbamoyl}benzoate, m.p. 165°, are obtained.

EXAMPLE 4

A solution of 1.3 g of methyl 4-{3[(benzo[1,3]dioxol-5-ylmethyl)carbamoyl]-4,5,6,7-tetrahydrobenzo[b]thiophen-2-ylcarbamoyl}benzoate, 100 ml of methanol and 30 ml of 1 N NaOH is stirred for 4 hours at 50°. Working-up is carried out in the customary manner and 4-{3[(benzo[1,3]dioxol-5-ylmethyl)carbamoyl]-4,5,6,7-tetrahydrobenzo[b]thiophen-2-ylcarbamoyl}benzoic acid, m.p. 259–261°, is obtained.

The following carboxylic acids are obtained in an analogous manner by hydrolysis of the esters obtained in Examples 1 and 2:

4-{3-[(benzo[1,3]dioxol-5-ylmethyl)carbamoyl]-5-methylthiophen-2-ylcarbamoyl}benzoic acid, hydrate, m.p. >270°;

4-{3-[(benzo[1,3]dioxol-5-ylmethyl)carbamoyl]-5,6-dimethylthiophen-2-ylcarbamoyl}benzoic acid;

4-{3-[(benzo[1,3]dioxol-5-ylmethyl)carbamoyl]-5-chlorothiophen-2-ylcarbamoyl}benzoic acid;

4-{3-[(benzo[1,3]dioxol-5-ylmethyl)carbamoyl]-4,5-cyclopentenothiophen-2-ylcarbamoyl}benzoic acid;

4-{3-[(benzo[1,3]dioxol-5-ylmethyl)carbamoyl]-4,5-cycloheptenothiophen-2-ylcarbamoyl}benzoic acid;

4-{3-[(benzo[1,3]dioxol-5-ylmethyl)carbamoyl]-5-ethylthiophen-2-ylcarbamoyl}benzoic acid, m.p. >270°;

4-{3-[(benzo[1,3]dioxol-5-ylmethyl)carbamoyl]-5-propylthiophen-2-ylcarbamoyl}benzoic acid;

4-{3-[(benzo[1,3]dioxol-5-ylmethyl)carbamoyl]-5-isopropylthiophen-2-ylcarbamoyl}benzoic acid, m.p. >270°;

4-{3-[(benzo[1,3]dioxol-5-ylmethyl)carbamoyl]-5-butylthiophen-2-ylcarbamoyl}benzoic acid, m.p. 245°;

4-[3-(benzylcarbamoyl-4,5,6,7-tetrahydrobenzo[b]thiophen-2-ylcarbamoyl]benzoic acid;

4-[3-(benzylcarbamoyl)-5-methylthiophen-2-ylcarbamoyl]benzoic acid;

4-[3-(benzylcarbamoyl)-5-isopropylthiophen-2-ylcarbamoyl]benzoic acid, m.p. 275–277°

4-[3-(benzylcarbamoyl)-5-chlorothiophen-2-ylcarbamoyl]benzoic acid;

4-[3-(benzylcarbamoyl)-4,5-cyclopentenothiophen-2-ylcarbamoyl]benzoic acid;

4-[3-(benzylcarbamoyl)-4,5-cycloheptenothiophen-2-ylcarbamoyl]benzoic acid;

4-[3-(benzylcarbamoyl)-5-ethylthiophen-2-ylcarbamoyl]benzoic acid;

4-{3-[(3-chloro-4-methoxybenzyl)carbamoyl]-4,5,6,7-tetrahydrobenzo[b]thiophen-2-ylcarbamoyl}benzoic acid;

4-{3-[(3-chloro-4-methoxybenzyl)carbamoyl]-5-methylthiophen-2-ylcarbamoyl}benzoic acid;

4-{3-[(3-chloro-4-methoxybenzyl)carbamoyl]-5-chlorothiophen-2-ylcarbamoyl}benzoic acid;

4-{3-[(3-chloro-4-methoxybenzyl)carbamoyl]-4,5-cyclopentenothiophen-2-ylcarbamoyl}benzoic acid;

4-{3-[(3-chloro-4-methoxybenzyl)carbamoyl]-4,5-cycloheptenothiophen-2-ylcarbamoyl}benzoic acid;

4-{3-[(3-chloro-4-methoxybenzyl)carbamoyl]-5-ethylthiophen-2-ylcarbamoyl}benzoic acid;

4-{3-[(3,4-dimethoxybenzyl)carbamoyl]-4,5,6,7-tetrahydrobenzo[b]thiophen-2-ylcarbamoyl}benzoic acid;

4-{3-[(3,4-dimethoxybenzyl)carbamoyl]-5-methylthiophen-2-ylcarbamoyl}benzoic acid, hydrate, m.p. >270°;

4-{3-[(3,4-dimethoxybenzyl)carbamoyl]-5-chlorothiophen-2-ylcarbamoyl}benzoic acid;

4-{3-[(3,4-dimethoxybenzyl)carbamoyl]-4,5-cyclopentenothiophen-2-ylcarbamoyl}benzoic acid;

4-{3-[(3,4-dimethoxybenzyl)carbamoyl]-4,5-cycloheptenothiophen-2-ylcarbamoyl}benzoic acid;

4-{3-[(3,4-dimethoxybenzyl)carbamoyl]-5-ethylthiophen-2-ylcarbamoyl}benzoic acid;
4-{3-[(4-fluorobenzyl)carbamoyl]-4,5,6,7-tetrahydrobenzo[b]thiophen-2-ylcarbamoyl}benzoic acid;
4-{3-[(4-fluorobenzyl)carbamoyl]-5-methylthiophen-2-ylcarbamoyl}benzoic acid;
4-{3-[(4-fluorobenzyl)carbamoyl]-5-chlorothiophen-2-ylcarbamoyl}benzoic acid;
4-{3-[(4-fluorobenzyl)carbamoyl]-4,5-cyclopentenothiophen-2-ylcarbamoyl)benzoic acid;
4-{3-[(4-fluorobenzyl)carbamoyl]-4,5-cycloheptenothiophen-2-ylcarbamoyl}benzoic acid;
4-[3-[(4-fluorobenzyl)carbamoyl]-5-ethylthiophen-2-ylcarbamoyl}benzoic acid;
4-(3-[(3-nitrobenzyl)carbamoyl]-4,5,6,7-tetrahydrobenzo[b]thiophen-2-ylcarbamoyl}benzoic acid;
4-{3-[(3-nitrobenzyl)carbamoyl]-5-methylthiophen-2-ylcarbamoyl}benzoic acid;
4-{3-[(3-nitrobenzyl)carbamoyl]-5-chlorothiophen-2-ylcarbamoyl}benzoic acid;
4-{3-[(3-nitrobenzoyl)carbamoyl]-4,5-cyclopentenothiophen-2-ylcarbamoyl}benzoic acid;
4-{3-[(3-nitrobenzyl)carbamoyl]-4,5-cycloheptenothiophen-2-ylcarbamoyl}benzoic acid;
4-{3-[(3-nitrobenzyl)carbamoyl]-5-ethylthiophen-2-ylcarbamoyl}benzoic acid;
4-[3-(phenethylcarbamoyl)-4,5,6,7-tetrahydrobenzo[b]thiophen-2-ylcarbamoyl]benzoic acid;
4-[3-(phenethylcarbamoyl)-5-methylthiophen-2-ylcarbamoyl]benzoic acid;
4-[3-(phenethylcarbamoyl)-5-chlorothiophen-2-ylcarbamoyl]benzoic acid;
4-[3-(phenethylcarbamoyl)-4,5-cyclopentenothiophen-2-ylcarbamoyl]benzoic acid;
4-[3-(phenethylcarbamoyl)-4,5-cycloheptenothiophen-2-ylcarbamoyl]benzoic acid;
4-[3-(phenethylcarbamoyl)-5-ethylthiophen-2-ylcarbamoyl]benzoic acid;
4-{3-[(benzo[1,3]dioxol-5-ylmethyl)carbamoyl]-4,5,6,7-tetrahydrobenzo[b]thiophen-2-ylcarbamoyl}cyclohexanecarboxylic acid, m.p. 265°;
4-{3-[(benzo[1,3]-dioxol-5-ylmethyl)carbamoyl]-5-methylthiophen-2-ylcarbamoyl}cyclohexanecarboxylic acid, sodium salt, dihydrate m.p. 130°;
4-{3-[(benzo[1,3]-dioxol-5-ylmethyl)carbamoyl]-5,6-dimethylthiophen-2-ylcarbamoyl}cyclohexanecarboxylic acid;
4-{3-[(benzo[1,3]-dioxol-5-ylmethyl)carbamoyl]-5-chlorothiophen-2-ylcarbamoyl}cyclohexanecarboxylic acid;
4-{3-[(benzo[1,3]-dioxol-5-ylmethyl)carbamoyl]-4,5-cyclopentenothiophen-2-ylcarbamoyl}cyclohexanecarboxylic acid;
4-{3-[(benzo[1,3]-dioxol-5-ylmethyl)carbamoyl]-4,5-cycloheptenothiophen-2-ylcarbamoyl}cyclohexanecarboxylic acid;
4-{3-[(benzo[1,3]dioxol-5-ylmethyl)carbamoyl]-5-ethylthiophen-2-ylcarbamoyl}cyclohexanecarboxylic acid, sodium salt, trihydrate, m.p. 133°;
4-[3-(benzylcarbamoyl)-4,5,6,7-tetrahydrobenzo[b]thiophen-2-ylcarbamoyl]cyclohexanecarboxylic acid;
4-[3-(benzylcarbamoyl)-5-methylthiophen-2-ylcarbamoyl]cyclohexanecartoxylic acid, m.p. 266°;
4-[3-(benzylcarbamoyl)-5-chlorothiophen-2-ylcarbamoyl]cyclohexanecarboxylic acid;
4-[3-(benzylcarbamoyl)-4,5-cyclopentenothiophen-2-ylcarbamoyl]cyclohexanecarboxylic acid;
4-[3-(benzylcarbamoyl)-4,5-cycloheptenothiophen-2-ylcarbamoyl]cyclohexanecarboxylic acid;
4-[3-(benzylcarbamoyl)-5-ethylthiophen-2-ylcarbamoyl]cyclohexanecarboxylic acid;
4-{3-[(3-chloro-4-methoxybenzyl)carbamoyl]-4,5,6,7-tetrahydrobenzo[b]thiophen-2-ylcarbamoyl}cyclohexanecarboxylic acid;
4-{3-[(3-chloro-4-methoxybenzyl)carbamoyl]-5-methylthiophen-2-ylcarbamoyl}cyclohexanecarboxylic acid;
4-{3-[(3-chloro-4-methoxyberizyl)carbamoyl]-5-chlorothiophen-2-ylcarbamoyl}cyclohexanecarboxylic acid;
4-{3-[(3-chloro-4-methoxybenzyl)carbamoyl]-4,5-cyclopentenothiophen-2-ylcarbamoyl}cyclohexanecarboxylic acid;
4-{3-[(3-chloro-4-methoxybenzyl)carbamoyl]-4,5-cycloheptenothiophen-2-ylcarbamoyl}cyclohexanecarboxylic acid;
4-{3-[(3-chloro-4-methoxybenzyl)carbamoyl]-5-ethylthiophen-2-ylcarbamoyl}cyclohexanecarboxylic acid;
4-{3-[(3,4-dimethoxybenzyl carbamoyl]-4,5,6,7-tetrahydrobenzo[b]thiophen-2-ylcarbamoyl}cyclohexanecarboxylic acid;
4-{3-[(3,4-dimethoxybenzyl)carbamoyl]-5-methylthiophen-2-ylcarbamoyl}cyclohexanecarboxylic acid;
4-{3-[(3,4-dimethoxybenzyl)carbamoyl]-5-chlorothiophen-2-ylcarbamoyl}cyclohexanecarboxylic acid;
4-{3-[(3,4-dimethoxybenzyl)carbamoyl]-4,5-cyclopentenothiophen-2-ylcarbamoyl}cyclohexanecarboxylic acid;
4-{3-[(3,4-dimethoxybenzyl) carbamoyl]-4,5-cycloheptenothiophen-2-ylcarbamoyl}cyclohexanecarboxylic acid;
4-{3-[(3,4-dimethoxybenzyl)carbamoyl]-5-ethylthiophen-2-ylcarbamoyl}cyclchexanecarboxylic acid;
4-{3-[(4-fluorobenzyl)carbamoyl]-4,5,6,7-tetrahydrobenzo[b]thiophen-2-ylcarbamoyl}cyclohexanecarboxylic acid;
4-{3-[(4-fluorobenzyl)carbamoyl]-5-methylthiophen-2-ylcarbamoyl}cyclohexanecaroxylic acid;
4-{3-[(4-fluorobenzyl)carbamoyl]-5-chlorothiophen-2-ylcarbamoyl}cyclohexanecaroxylic acid;
4-{3-[(4-fluorobenzyl)carbamoyl]-4,5-cyclopentenothiophen-2-ylcarbamoy}cyclohexanecarboxylic acid;
4-{3-[(4-fluorobenzyl)carbamoyl]-4,5-cycloheptenothiophen-2-ylcarbamoyl}cyclohexanecarboxylic acid;
4-{3-[(4-fluorobenzyl)carbamoyl]-5-ethylthiophen-2-ylcarbamoyl}cyclohexanecarboxylic acid;
4-{3-[(3-nitrobenzyl)carbamoyl]-4,5,6,7-tetrahydrobenzo[b]thiophen-2-ylcarbamoyl}cyclohexanecarboxylic acid;
4-{3-[(3-nitrobenzyl)carbamoyl]-5-methylthiophen-2-ylcarbamoyl}cyclohexanecarboxylic acid;
4-{3-[(3-nitrobenzyl)carbamoyl]5-chlorothiophen-2-ylcarbamoyl}cyclohexanecarboxylic acid;
4-{3-[(3-nitrobenzyl)carbamoyl]-4,5-cyclopentenothiophen-2-ylcarbamoyl}cyclohexanecarboxylic acid;
4-{3-[(3-nitrobenzyl)carbamoyl]-4,5-cycloheptenothiophen-2-ylcarbamoyl}cyclohexanecarboxylic acid;
4-{3-[(3-nitrobenzyl)carbamoyl]-5-ethylthiophen-2-ylcarbamoyl}cyclohexanecarboxylic acid;
4-[3-(phenethylcarbamoyl)-4,5,6,7-tetrahydrobenzo[b]thiophen-2-ylcarbamoyl]cyclohexanecarboxylic acid;

4-[3-(phenethylcarbamoyl)-5-methylthiophen-2-ylcarbamoyl]cyclohexanecarboxylic acid;

4-[3-(phenethylcarbamoyl)-5-chlorothiophen-2-ylcarbamoyl]cyclohexanecarboxylic acid;

4-[3-(phenethylcarbamoyl)-4,5-cyclopentenothiophen-2-ylcarbamoyl]cyclohexanecarboxylic acid;

4-[3-(phenethylcarbamoyl)-4,5-cycloheptenothiophen-2-ylcarbamoyl]cyclohexanecarboxylic acid;

4-[3-(phenethylcarbamoyl)-5-ethylthiophen-2-ylcarbamoyl]cyclohexanecarboxylic acid.

Following compounds are obtained in an analogous manner

4-[3-(benzylcarbamoyl)-5-isopropylthiophen-2-ylcarbamoyl]cyclohexanecarbcxylic acid, m.p. 198°;

4-[3-(benzylcarbamoyl)-5-propylthiophen-2-ylcarbamoyl]benzoic acid, m.p. 268°;

4-{3-[(benzo[1,3]-dioxol-5-ylmethyl)carbamoyl]-5-isopropylthiophen-2-ylcarbarmoyl}cyclohexane carboxylic acid, sodium salt, m.p. 240°.

EXAMPLE 5

A solution of 4-{3-[(3-nitrobenzyl)carbamoyl]-5-ethylthiophen-2-ylcarbamoyl}cyclohexanecarboxylic acid in methanol is hydrogenated in the presence of Raney nickel. The catalyst is filtered off and the solution is concentrated. After recrystallization, 4-{3-[(3-aminobenzyl)carbamoyl]-5-ethylthiophen-2-ylcarbamoyl}cyclohexanecarboxylic acid is obtained.

EXAMPLE 6

Analogously to Example 1, the compound 4-{3-[(benzo[1,3]-dioxol-5-ylmethyl)carbamoyl]-4,5,6,7-tetrahydrobenzo[b]thiophen-2-ylcarbamoyl}-3-nitrobenzene is obtained by reacting N-(benzo[1,3]dioxol-5-ylmethyl)-2-amino-4,5,6,7-tetrahydrobenzo[b]thiophene-3-carboxamide and 3-nitrobenzoyl chloride.

4-{3-[(3,4-dimethoxybenzyl)carbamoyl]-5-methylthiophen-2-ylcarbamoyl}-3-nitrobenzene is obtained in an analogous manner.

Analogously to Example 5, the following compounds are obtained by catalytic reduction of the 3-nitro derivatives 4-{3-[(benzo[1,3]-dioxol-5-ylmethyl)carbamoyl]-4,5,6,7-tetrahydrobenzo[b]thiophen-2-ylcarbamoyl}-3-aminobenzene and 4-{3-[(3,4-dimethoxybenzyl)carbamoyl]-5-methylthiophen-2-ylcarbamoyl}-3-aminobenzene.

Reaction with equivalent amounts of methylsulphonyl chloride and pyridine in dichloromethane gives 4-{3-[(benzo[1,3]dioxol-5-ylmethyl)carbamoyl]-4,5,6,7-tetrahydrobenzo[b]thiophen-2-ylcarbamoyl}-2-methylsulphonamidobenzene and 4-{3-[(3,4-dimethoxybenzyl)carbamoyl]-5-methylthiophen-2-ylcarbamoyl}-3-methylsulphonamidobenzene.

The following Examples relate to pharmaceutical formulations:

Example A: Injection Vials

A solution of 100 g of an active ingredient of the formula I and 5 g of disodium hydrogen phosphate in 3 l of doubly distilled water is adjusted to pH 6.5 with 2 N hydrochloric acid, st-erile-filtered, filled into injection vials and lyophilized under sterile conditions and the vials are closed under sterile conditions. Each injection vial contains 5 mg of active ingredient.

Example B: Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

Example C: Solution

A solution is prepared from 1 g of an active ingredient of the formula I, 9.38 g of $NaH_2PO_4.12H_2O$, 28.48 g of $Na_2HPO_4.12H_2O$ and 0.1 g of benzalkonium chloride in 940 ml of doubly distilled water. It is adjusted to pH 6.8, made up tc) 1 l and sterilized by irradiation. This solution can be used in the form of eye drops.

Example D: Ointment 500 mg of an active ingredient of the formula I is mixed with 99.5 g of vaseline under aseptic conditions.

Example E: Tablets

A mixture of 1 kg of active ingredient of the formula I, 4 kg of lactose, 1.2 kg of potato starch, 0.2 kg of talc and 0.1 kg of magnesium stearate is compressed in the customary manner to give tablets, so that each table contains 10 mg of active ingredient.

Example F: Sugar-coated Tablets

Tablets are produced by compression analogously to Example E and are then covered in the customary manner with a coat comprising sucrose, potato starch, talc, tragacanth and colour.

Example G: Capsules 2 kg of active ingredient of the formula I are filled in the customary manner into hard gelatine capsules so that each capsule contains 20 mg of the active ingredient.

Example H: Ampoules

A solution of 1 kg of active ingredient of the formula I in 60 l of doubly distilled water is sterile-filtered, filled into ampoules and lyophilized under sterile conditions and the ampoules are closed under sterile conditions. Each ampoule contains 10 mg of active ingredient.

Example I: Inhalation Spray 14 g of active ingredient of the formula I are dissolved in 10 l of isotonic NaCl solution and the solution is filled into commercial spray vessels having a pump mechanism. The solution can be sprayed into the mouth or nose. One spray actuation (about 0.1 ml) corresponds to a dose of about 0.14 mg.

What is claimed is:

1. Compounds of the formula I

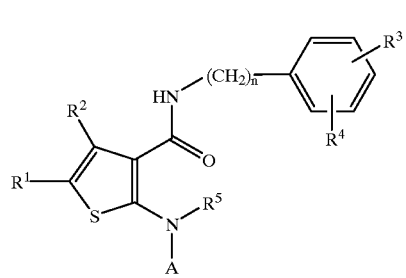

where $R^1$ and $R^2$, independently of one another, are each H, A, OA, alkenyl, alkynyl, $CF_3$ or Hal, one of the radicals $R^1$ or $R^2$ always being≠H, $R^1$ and $R^2$ together are also alkylene having 3–5 C atoms, $R^3$ and $R^4$, independently of one another, are each H, A, OA, $NO_2$, $NH_2$ or Hal, $R^3$ and $R^4$ together are also $-O-CH_2-CH_2-$, $-O-CH_2-O-$ or $-O-CH_2-CH_2-O-$, A and A', independently of one another, are each H or alkyl having 1 to 6 C atoms, $R^5$ is $-X-Y$, X is CO, CS or $SO_2$, Y is a saturated or unsaturated 5- to 7-membered isocyclic or heterocyclic ring which is unsubstituted or monosubstituted or disubstituted by COOH, COOA, $CONH_2$, CONAA', CONHA, CN, $NHSO_2A$, $N(SO_2A)_2$ or $SO_2A$, Hal is F, Cl, Br or I and n is 0, 1, 2 or 3, and their physiologically acceptable salts excluding the compound 2-benzoylamino- 4,5,6,7-tetrahydro-benzo[b]thiophen-3-carboxylic acid N-phenylamide.

2. Compounds of the formula I according to claim 1

(a) 4-{3-[(benzo[1,3]dioxol-5-ylmethyl)carbamoyl]-4,5,6,7-tetrahydrobenzo[b]thiophen-2-ylcarbamoyl}-benzoic acid;

(b) 4-[3-(benzylcarbamoyl)-5-methylthiophen-2-ylcarbamoyl]benzoic acid;

(c) 4-{3-[(benzo[1,3]dioxol-5-ylmethyl)carbamoyl]-5-methylthiophen-2-ylcarbamoyl}benzoic acid;

(d) 4-{3-[(benzo[1,3]dioxol-5-ylmethyl)carbamoyl]-5-methylthiophen-2-ylcarbamoyl}cyclohexanecarboxylic acid;

(e) 4-{3-[(benzo[1,3]dioxol-5-ylmethyl)carbamoyl]-4,5,6,7-tetrahydrobenzo[b]thiophen-2-ylcarbamoyl}benzoic acid;

(f) 4-{3-[(3-chloro-4-methoxybenzyl)carbamoyl]-4,5,6,7-tetrahydrobenzo[b]thiophen-2-ylcarbamoyl}benzoic acid;

(g) 4-{3-[(3-chloro-4-methoxybenzyl)carbamoyl]-5-methylthiophen-2-ylcarbamoyl}benzoic acid;

(h) 4-{3-[(3-chloro-4-methoxybenzyl)carbamoyl]-5-ethylthiophen-2-ylcarbamoyl}benzoic acid;

(i) 4-{3-[(3-chloro-4-methoxybenzyl)carbamoyl]-4,5,6,7-tetrahydrobenzo[b]thiophen-2-ylcarbamoyl}-cyclohexanecarboxylic acid;

(k) 4-{3-[(3-chloro-4-methoxybenzyl)carbamoyl]-5-methylthiophen-2-ylcarbamoyl}-cyclohexanecarboxylic acid and their physiologically acceptable salts.

3. Process for the preparation of compounds of the formula I according to claim 1 and their salts, characterized in that a) a compound of the formula II

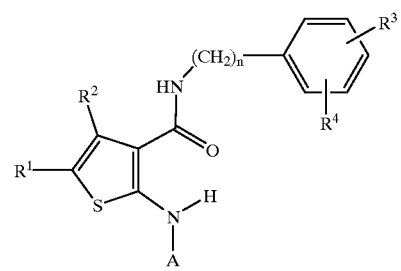

wherein
$R^1$, $R^2$, $R^3$, $R^4$ and n have the stated meanings,
is reacted with a compound of the formula III $$L-R^5 \qquad III$$

wherein $R^5$ has the stated meaning and
L is Cl, Br, I, OH or an OH group rendered reactive by esterification, or b) a compound of the formula IV

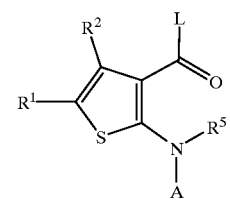

wherein
$R^1$, $R^2$, $R^5$ and A have the stated meanings and L is Cl, Br, I, OH or an OH group rendered reactive by esterification,
is reacted with a compound of the formula V

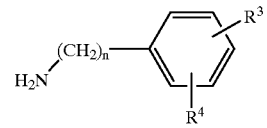

wherein
$R^3$, $R^4$ and n have the stated meanings, or c) in a compound of the formula I, a radical $R^3$, $R^4$ and/or $R^5$ is converted into another radical $R^3$, $R^4$ and/or $R^5$ by hydrolysing an ester or reducing a nitro group, and/or that an acidic compound of the formula I is converted into one of its salts by treatment with a base.

4. A process for the preparation of a pharmaceutical formulation comprising combining of at least one compound of formula I according to claim 1 or a physiologically acceptable salt thereof with at least one solid, liquid or semiliquid vehicle or excipient.

5. A pharmaceutical formulation comprising at least one compound of formula I according to claim 1 or a physiologically acceptable salt thereof.

6. A method of treating disease in a human subject comprising administering a compound of formula I according to claim 1 or a physiologically acceptable salt thereof to a human subject.

7. A pharmaceutical formulation according to claim 5, further comprising at least one pharmaceutically acceptable excipient.

8. A method of treating disease in a subject comprising administering a phosphodiesterase V inhibitor to the subject wherein the phosphodiesterase V inhibitor is a compound of formula I according to claim 1.

9. A method according to claim 6 wherein the subject is treated for diseases of the cardiovascular system or for disturbances of potency.

10. A method according to claim 8 wherein the subject is treated for diseases of the cardiovascular system or for disturbances of potency.

11. A phosphodiesterase V inhibitor of formula I according to claim 1.

12. A process for the preparation of a pharmaceutical formulation comprising combining of at least one compound according to claim 2 or a physiologically acceptable salt thereof with at least one solid, liquid or semiliquid vehicle or excipient.

13. A pharmaceutical formulation comprising at least one compound according to claim 2 or a physiologically acceptable salt thereof.

14. A method of treating disease in a human subject comprising administering a compound according to claim 2 or a physiologically acceptable salt thereof to a human subject.

15. A pharmaceutical formulation according to claim 16, further comprising at least one pharmaceutically acceptable excipient.

16. A method of treating disease in a subject comprising administering a phosphodiesterase V inhibitor to the subject wherein the phosphodiesterase V inhibitor is a compound according to claim 2.

17. A method according to claim 14 wherein the subject is treated for diseases of the cardiovascular system or for disturbances of potency.

18. A method according to claim 16 wherein the subject is treated for diseases of the cardiovascular system or for disturbances of potency.

19. A phosphodiesterase V inhibitor according to claim 2.

* * * * *